US012746035B2

(12) United States Patent
Krishnamoorthy et al.

(10) Patent No.: US 12,746,035 B2
(45) Date of Patent: Sep. 29, 2026

(54) ACCESS PORTS FOR USE WITH SURGICAL ROBOTS

(71) Applicant: Conmed Corporation, Largo, FL (US)

(72) Inventors: Mahesh Krishnamoorthy, Parker, CO (US); George R. Trutza, East Greenwich, RI (US); Michael Funk, Broomfield, CO (US)

(73) Assignee: Conmed Corporation, Largo, FL (US)

(*) Notice: Subject to any disclaimer, the term of this patent is extended or adjusted under 35 U.S.C. 154(b) by 84 days.

(21) Appl. No.: 18/692,615

(22) PCT Filed: Nov. 11, 2022

(86) PCT No.: PCT/US2022/049726
§ 371 (c)(1),
(2) Date: Mar. 15, 2024

(87) PCT Pub. No.: WO2023/086587
PCT Pub. Date: May 19, 2023

(65) Prior Publication Data

US 2024/0374285 A1 Nov. 14, 2024

Related U.S. Application Data

(60) Provisional application No. 63/279,621, filed on Nov. 15, 2021.

(51) Int. Cl.
*A61B 17/00* (2006.01)
*A61B 17/34* (2006.01)
*A61B 90/00* (2016.01)

(52) U.S. Cl.
CPC .......... *A61B 17/3423* (2013.01); *A61B 90/03* (2016.02); *A61B 2017/0042* (2013.01);
(Continued)

(58) Field of Classification Search
CPC ............... A61B 17/34; A61B 17/3423; A61M 2039/0276; A61M 2039/0279
See application file for complete search history.

(56) References Cited

U.S. PATENT DOCUMENTS 8,795,223 B2 * 8/2014 Stearns ............. A61B 17/3462 604/167.03
10,905,463 B2 * 2/2021 Silver ..................... A61M 1/71
(Continued)

FOREIGN PATENT DOCUMENTS

EP 1516592 A2 3/2005
WO 2014/052532 A1 4/2014
(Continued)

OTHER PUBLICATIONS

Australian Examination Report dated Nov. 30, 2024, issued during the prosecution of AU 2022384281.
(Continued)

*Primary Examiner* — Nicholas W Woodall
(74) *Attorney, Agent, or Firm* — Troutman Pepper Locke LLP; Scott D. Wofsy

(57) ABSTRACT

In accordance with at least one aspect of this disclosure, an access port for performing an endoscopic surgical procedure in a surgical cavity of a patient includes a proximal housing portion. The proximal housing portion includes, a central lumen providing instrument access to the surgical cavity and an engagement housing operatively associated with a proximal end of the proximal housing portion and having a circumferential engagement area formed therein that is adapted and configured to releasably accept a grasping member of a surgical robot. An elongated tubular body portion extends from the proximal housing portion in communication with the central lumen.

7 Claims, 7 Drawing Sheets

(52) U.S. Cl.
CPC ............... *A61B 2017/00477* (2013.01); *A61B 2017/00831* (2013.01); *A61B 2017/3425* (2013.01); *A61B 2090/035* (2016.02)

(56) References Cited

U.S. PATENT DOCUMENTS

| | | | | |
|---|---|---|---|---|
| 2016/0220271 | A1* | 8/2016 | Mastri ................. | A61M 13/003 |
| 2017/0086930 | A1* | 3/2017 | Thompson ......... | A61B 17/3476 |
| 2018/0049824 | A1 | 2/2018 | Harris et al. | |
| 2018/0168689 | A1* | 6/2018 | Beckman ........... | A61B 17/3498 |
| 2018/0177557 | A1* | 6/2018 | Kapadia ................. | A61B 17/00 |
| 2020/0015853 | A1* | 1/2020 | Hall ................... | A61B 17/3462 |
| 2020/0305928 | A1* | 10/2020 | Thompson ......... | A61B 17/3421 |
| 2021/0137611 | A1* | 5/2021 | Traina ................ | A61B 17/3462 |
| 2022/0119734 | A1 | 4/2022 | Granier et al. | |
| 2024/0325048 | A1* | 10/2024 | Thompson ......... | A61B 17/3474 |

FOREIGN PATENT DOCUMENTS

| | | | |
|---|---|---|---|
| WO | 2019/136062 | A1 | 7/2019 |
| WO | 2020/005612 | A1 | 1/2020 |
| WO | 2022119734 | A1 | 6/2022 |

OTHER PUBLICATIONS

International Search Report issued in PCT/US2022/049726, mailed Mar. 31, 2023.

European Office Action issued in EP 22840370.5, mailed Sep. 3, 2025.

Canadian Office Action dated Jul. 22, 2025, issued during the prosecution on Canadian Patent Application No. 3231377.

IPRP dated May 2, 2024, issued during the prosecution of PCT/US2022/049726.

* cited by examiner

ACCESS PORTS FOR USE WITH SURGICAL ROBOTS

CROSS-REFERENCE TO RELATED APPLICATIONS

This application is a U.S. National Phase Application filed under 35 U.S.C. § 371, based on International Patent Application No. PCT/US2022/049726, filed Nov. 11, 2022, which claims benefit of priority to U.S. Provisional Patent Application No. 63/279,621, filed on Nov. 15, 2021, the content of which is incorporated by reference herein in its entirety.

FIELD

The subject disclosure is directed to endoscopic surgery, and more particularly, to a surgical gas delivery system for gas sealed insufflation and recirculation having trocars compatible for use with surgical robots.

BACKGROUND

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal cavity with a pressurized fluid, such as carbon dioxide, to create an operating space, which is referred to as a pneumoperitoneum. The insufflation can be carried out by a surgical access device, such as a trocar, equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, often using a separate inserter or obturator placed therein. Following insertion, the obturator is removed, and the trocar allows access for instruments to be inserted into the abdominal cavity. Typical trocars provide a pathway to insufflate the cavity, so that a surgeon has an open interior space in which to work.

The trocar must also provide a way to maintain the pressure within the cavity by sealing between the trocar and the surgical instrument being used, while still allowing at least a minimum amount of freedom of movement for the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas from the abdominal cavity. These sealing mechanisms often comprise a duckbill-type valve made of a relatively pliable material, to seal around an outer surface of surgical instruments passing through the trocar.

SurgiQuest, Inc., a wholly owned subsidiary of ConMed Corporation has developed unique gas sealed surgical access devices that permit ready access to an insufflated surgical cavity without the need for conventional mechanical valve seals, as described, for example, in U.S. Pat. Nos. 7,854,724 and 8,795,223. These access devices are constructed from several nested components including an inner tubular body portion and a coaxial outer tubular body portion. The inner tubular body portion defines a gas sealed central lumen for introducing conventional laparoscopic or endoscopic surgical instruments to the surgical cavity of a patient and the outer tubular body portion defines an annular lumen surrounding the inner tubular body portion for delivering insufflation gas to the surgical cavity of the patient and for facilitating periodic sensing of abdominal pressure.

Surgical robotics manufacturers are exploring various configurations and approaches to implementing robotic-assisted surgery, whereby surgical robots are able to interact with trocars, to insert, manipulate, and/or remove the trocars during a procedure. Currently, there remains a need in the art for trocars, gas sealed trocars, and access ports compatible with surgical robots. The present disclosure provides a solution for this need.

SUMMARY

In accordance with at least one aspect of this disclosure, an access port for performing an endoscopic surgical procedure in a surgical cavity of a patient includes a proximal housing portion. The proximal housing portion includes a central lumen providing instrument access to the surgical cavity, wherein the proximal housing portion defined an interior plenum. An engagement housing is operatively associated with a proximal end of the proximal housing portion and having a circumferential engagement area formed therein that is adapted and configured to releasably accept a grasping member of a surgical robot. A seal is housed within the interior plenum, wherein the engagement housing is proximal relative to the interior plenum and to the seal. An elongated tubular body portion extends from the proximal housing portion in a distal direction, in communication with the central lumen.

In embodiments, the engagement area can have an engagement surface defining a shape that is configured to receive the grasping member of the surgical robot with a surface of the grasping member flush with the engagement surface within the engagement housing. In certain embodiments, the engagement housing includes a protrusion such that the circumferential engagement area extends only partially circumferentially around the engagement housing, where the engagement housing has a generally c-shaped profile in cross-section. In certain such embodiments, the engagement housing can be configured to accept a corresponding c-shaped grasping member of the surgical robot, or the engagement housing can be shaped to correspond to any shape of the grasping member of the surgical robot.

In certain embodiments, the engagement housing is formed integral with the proximal housing portion, where the engagement housing is defined in a cover configured to attach to the proximal housing portion and form a fixed relationship with the proximal housing portion. In certain embodiments, the engagement housing is defined in a cover configured to attach to the proximal housing portion and is configured to rotate relative to the proximal housing portion. In certain such embodiments, the proximal housing portion can further include a stopper configured to prohibit rotation of the engagement housing relative to the proximal housing portion beyond the stopper. In embodiments, the stopper can be a detent.

The engagement housing further includes an attachment feature configured to engage a proximal end of an obturator passing through the central lumen. In embodiments, the proximal housing portion further includes a sound dampener disposed in the central lumen, where the sound dampener can include foam material configured to dampen air sounds in the central lumen.

In certain embodiments, the seal can include a ring jet assembly that is adapted and configured to accelerate pressurized gas delivered into the proximal housing portion to form a gaseous seal within a region of the tubular body portion so as to maintain a stable pressure in the surgical cavity. In certain embodiments, the seal can include a mechanical seal that is adapted and configured to prevent egress of insufflation gas from the surgical cavity.

In embodiments, the engagement housing is defined in a cover configured to attach to the proximal housing portion, the cover having one or more castellations extending distally therefrom configured to engage one or more detents in the proximal housing portion around the central lumen to retain the cover to the proximal housing portion.

In accordance with at least one aspect of this disclosure, a gas sealed access port for performing an endoscopic surgical procedure in a surgical cavity of a patient includes a proximal housing. The proximal housing portion includes a central lumen providing gas sealed access to the surgical cavity, an inlet path for communicating with a source of pressurized gas, a tapered neck portion and an interior cavity accommodating a seal including an annular jet assembly for receiving pressurized gas from the inlet path to generate a gaseous seal within the tapered neck portion to maintain a stable pressure within the surgical cavity. An engagement housing is operatively associated with a proximal end of the proximal housing portion and having a circumferential engagement area formed therein that is adapted and configured to releasably accept a grasping member of a surgical robot. An elongated tubular body extends distally from the tapered neck portion of the proximal housing in communication with the central lumen. The engagement housing can be the same or similar to that as described above.

In accordance with at least one aspect of this disclosure, an engagement housing for an access port for performing an endoscopic surgical procedure in a surgical cavity of a patient can include a cover configured to seat within a proximal housing of the access port. In embodiments, the cover can define an engagement area disposed at least partially circumferentially around an outer periphery of the cover configured to releasably accept a grasping member of a surgical robot. The cover can also include one or more castellations extending distally therefrom configured to engage one or more detents in the proximal housing of the access port to retain the cover to the proximal housing.

These and other features of the embodiments of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION OF THE PREFERRED EMBODIMENTS

Figure 1:
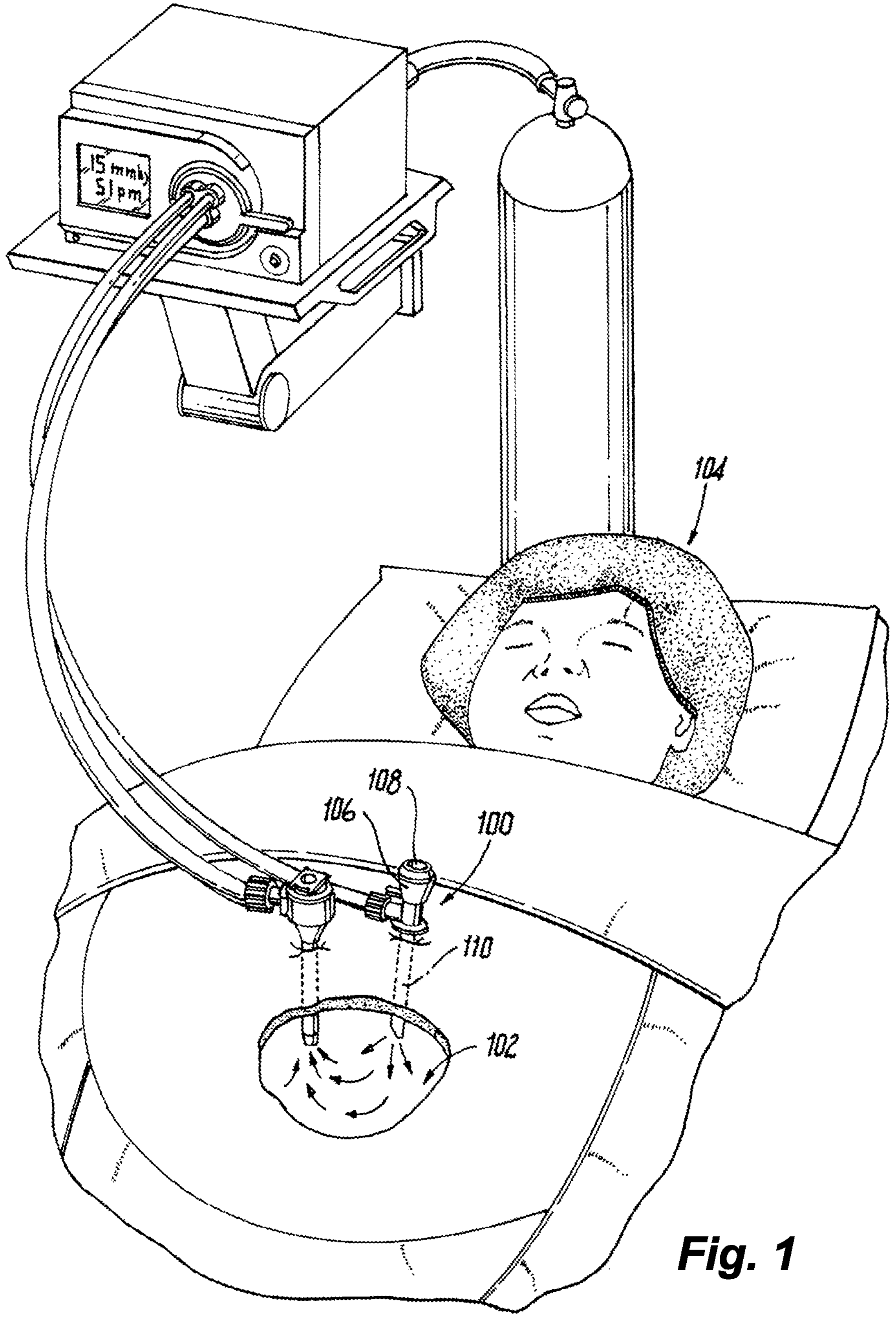
FIG. 1 is a perspective view of a surgical procedure in accordance with this disclosure, showing an access port disposed in a surgical cavity of a patient.

Reference will now be made to the drawings wherein like reference numerals identify similar structural features or aspects of the subject disclosure. For purposes of explanation and illustration, and not limitation, an illustrative view of an embodiment of an access port in accordance with the disclosure is shown in FIG. 1 and is designated generally by reference character 100. Other embodiments and/or aspects of this disclosure are shown in FIGS. 2-13.

Today the surgical robotics market is faced with a number of newcomers that are exploring various configurations and approaches to robotic-assisted surgery. Certain sealed trocars and access ports, for example as provided in commonly assigned U.S. Pat. No. 8,795,223 issued Aug. 5, 2014, U.S. Pat. No. 10,905,463, issued Feb. 2, 2021, U.S. Pat. No. 11,399,866, issued Aug. 2, 2022, and U.S. Pat. No. 11,039,857 issued Jun. 22, 2021, which are incorporated herein by reference in their entirety, have the ability to maintain a stable pneumoperitoneum, constant smoke evacuation and easy instrument insertion and withdrawal. Surgical robotics manufacturers would benefit from access ports having the benefits and functionality as those described and incorporated herein, that are compatible with said robotics, without modification by an end user. Embodiments of access ports as described herein will allow for the different configurations of surgical robots to work effectively with said access ports.

Figure 2:
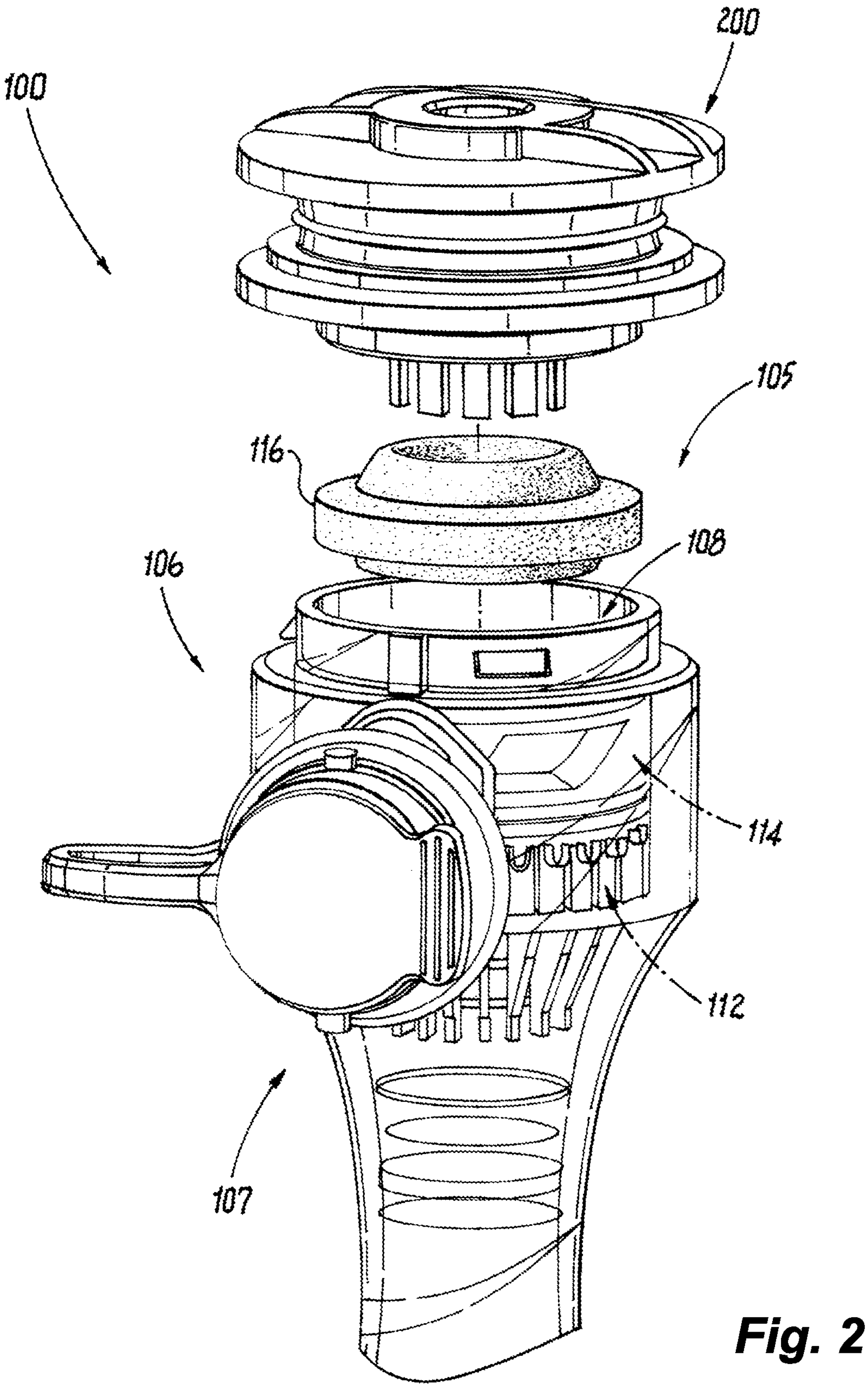
FIG. 2 is an exploded perspective view of the access port of the FIG. 1, showing an embodiment of a proximal housing portion.

In accordance with at least one aspect of this disclosure, as shown in FIGS. 1 and 2, an access port 100 for performing an endoscopic surgical procedure in a surgical cavity 102 of a patient 104 includes a proximal housing portion 106. The proximal housing portion 106 includes a proximal 105 end and distal end 107, a central lumen 108 providing instrument access to the surgical cavity 102 and an elongated tubular body portion 110 extends from the distal end 107 of the proximal housing portion 106 in communication with the central lumen 108. In certain embodiments, as shown in FIG. 2, the proximal housing portion 106 can define an interior plenum 112 housing a ring jet assembly 114 (e.g., similar to jet assembly 64 of U.S. Pat. No. 10,905,463) that is adapted and configured to accelerate pressurized gas delivered into the proximal housing portion 106 to form a gaseous seal within a region of the tubular body 110 portion so as to maintain a stable pressure in the surgical cavity 102. In certain embodiments, the proximal housing portion 106 can define an interior chamber housing a mechanical seal that is adapted and configured to prevent egress of insufflation gas from the surgical cavity 102, for example as in a conventional or standard trocar including a valve seal, a duckbill seal, septum seal or the like. Regardless of whether a gaseous seal or a mechanical seal is used, the engagement housing is proximal relative to the interior plenum/chamber and to the seal. In embodiments, the proximal housing portion 106 further includes a sound dampener 116 disposed in the central lumen 108, where the sound dampener 116 can include foam material configured to dampen air sounds in the central lumen 108.

Figure 3:
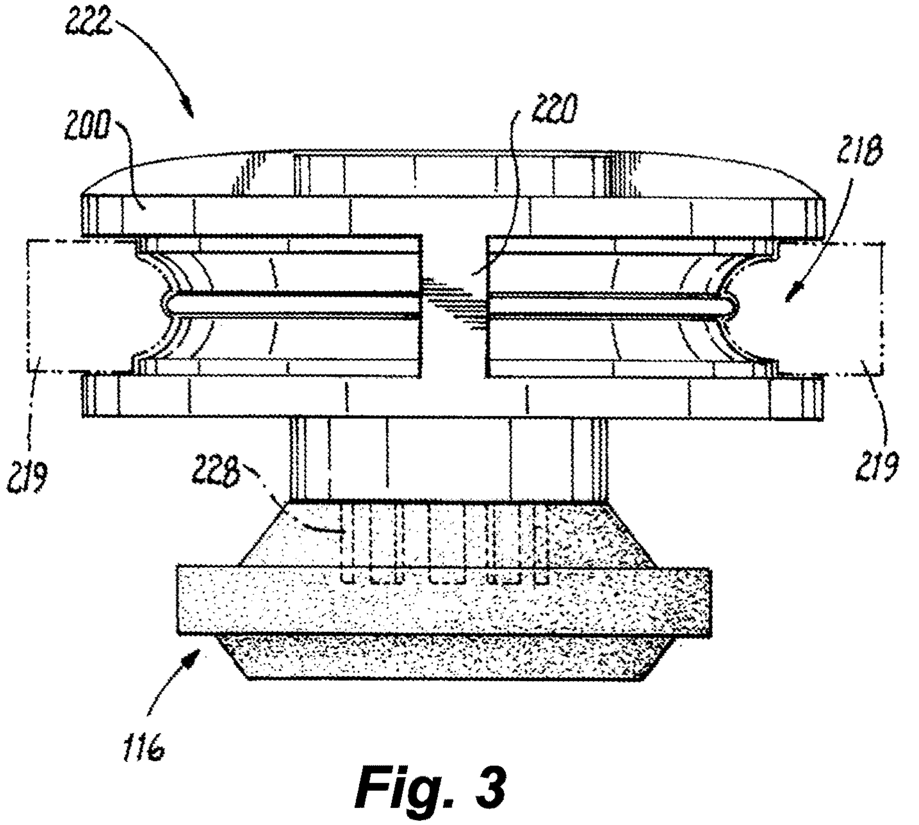
FIG. 3 is a side perspective view of an embodiment of an engagement housing of the access port of FIG. 1, showing an engagement area of the engagement housing.
Figure 4:
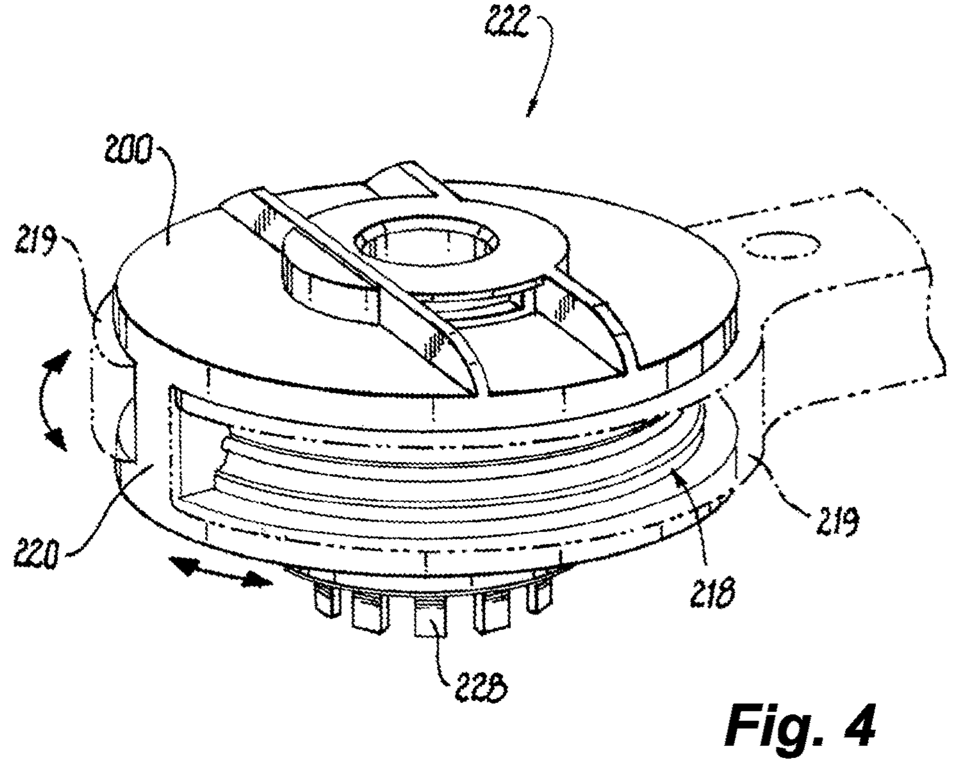
FIG. 4 is a side elevation view of the engagement housing of FIG. 3.
Figure 5:
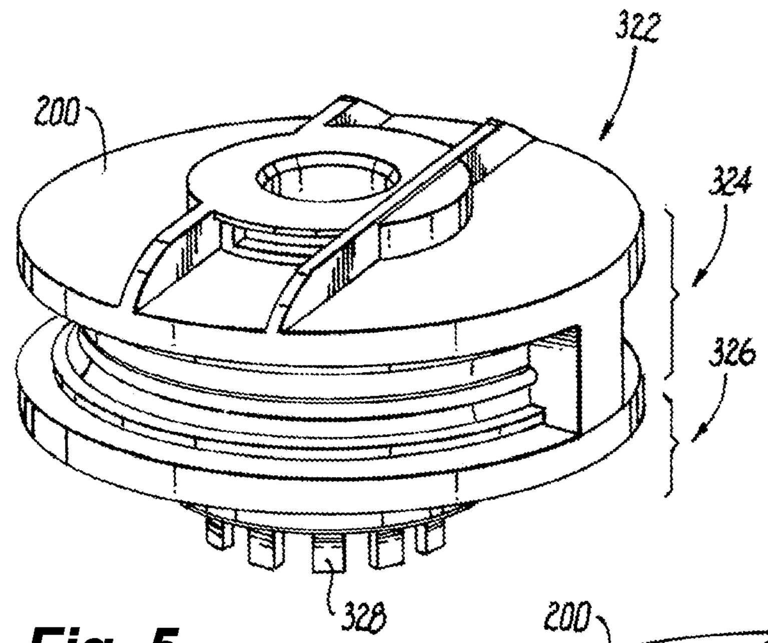
FIG. 5 is a side perspective view of an embodiment of an engagement housing of the access port of FIG. 1, showing an upper and lower portion of the engagement housing.

Referring now to FIGS. 3-5, an engagement housing 200 can be operatively associated with the proximal end 105 of the proximal housing portion 106 and having a circumferential engagement area 218 formed therein that is adapted and configured to releasably accept a grasping member of a surgical robot. In embodiments, such as shown, the engagement area 218 can be configured to allow the grasping member of the surgical robot to sit flush within the engagement housing 200. The engagement area has an engagement surface that defines a shape that is an inverted version of the shape of the surface of the grasping member, which allows the engagement surface to sit flush with the surface of the grasping member within the engagement housing. This flush engagement is indicated in FIGS. 3-4 with the broken lines indicating the flush engagement of the grasping member 219 in the engagement area 218 in FIG. 3. In embodiments, the engagement area 218 can facilitate the mating of the surgical robot's handle with the access port 100 to result in the motion and articulation of the access port 100 via the controls of the surgical robot. As shown in FIGS. 3-4, the engagement housing 200 and corresponding engagement area 218 can be designed, configured, and adapted to provide a standardized orientation of engagement housing 200 with respect to a given robotic grasping member.

In certain embodiments, the engagement housing 200 includes a protrusion 220 such that the circumferential engagement area 218 extends only partially circumferentially around the engagement housing 200. In this case, the engagement housing 200 and engagement area 218 can have a generally c-shaped profile in cross-section. In certain such embodiments then, the engagement housing 200 can be configured to accept a corresponding c-shaped grasping member of the surgical robot, though it is possible the engagement housing 200 can be shaped to correspond to any shape of any grasping member of a given surgical robot.

In certain embodiments, the protrusion 218 can act as leading edge for the engagement housing 200 when accepting the grasping member of the surgical robot, where the protrusion 220 can be oriented so as to prevent interference from a tube set during actuation of the access port 100. In certain embodiments, such as shown in FIG. 3-4, the engagement housing 200 can be defined in a cover 222 configured to attach to the proximal housing portion 106 and form a fixed relationship with the proximal housing portion 106, where the engagement housing 200 and/or cover 222 cannot rotate relative to the proximal housing portion 106. In certain embodiments, the engagement housing 200 can be integral with the proximal housing portion 106.

In certain embodiments, such as shown in FIG. 5, the engagement housing can be defined in a cover 322, wherein an upper portion 324 includes the engagement area 218, and a lower portion 326 is configured to attach to the proximal housing portion 106. The upper portion 324 can rotate or swivel relative to the lower portion 326 and/or the proximal housing portion 106. In this case, the lower portion 326 and/or the proximal housing portion 106 can further include a stopper configured to prohibit rotation of the upper portion 324 relative to the lower portion 326 and/or the proximal housing portion 106 beyond the stopper, and to lock the upper portion 324 in place. For example, it may be beneficial to provide some flexibility in the location of the protrusion 220 so as to account for surgeon preference or to prevent obstruction by the tube set during a surgical procedure. In embodiments, the stopper can be or include a detent, as described in further detail below with reference to FIGS. 10-13.

In embodiments, such as shown in FIGS. 3-5, the cover 222 can include one or more castellations 228 extending distally therefrom configured to engage one or more detents in the proximal housing portion 106 around the central lumen 108 to retain the cover 222 to the proximal housing portion 106 (e.g., as shown in FIGS. 3-4), or the castellations 328 can extend distally from the lower portion 326 of the cover 322 (e.g., as shown in FIG. 5).

Figure 6:
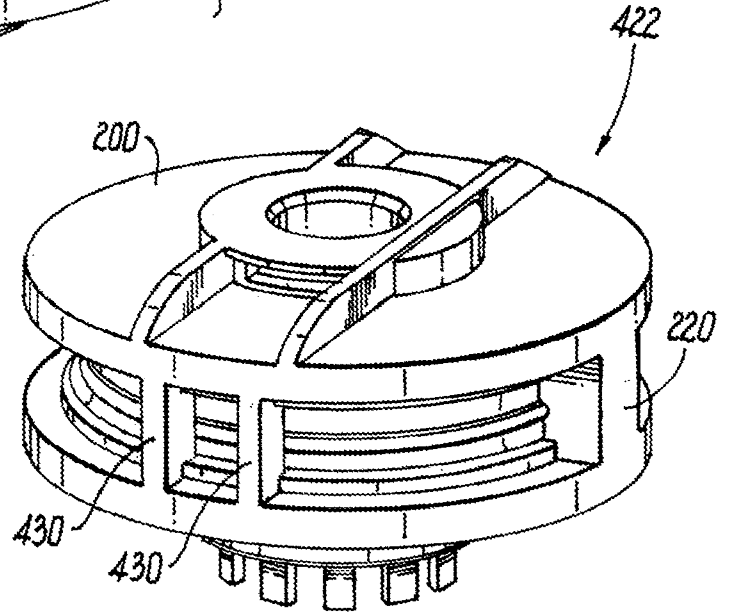
FIG. 6 is a side elevation view of an embodiment of an engagement housing of the access port of FIG. 1, showing an engagement area of the engagement housing having clamping features.
Figure 7:
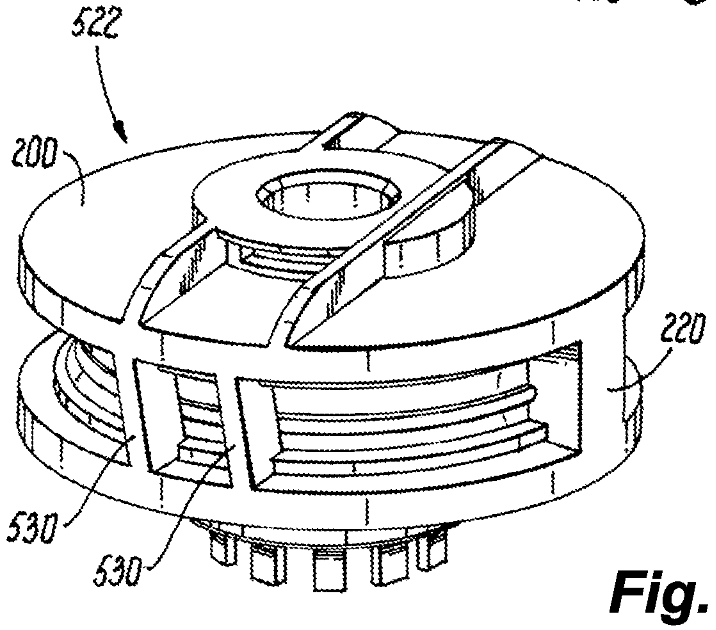
FIG. 7 is a side elevation view of an embodiment of an engagement housing of the access port of FIG. 1, showing an engagement area of the engagement housing having clamping features.

In certain embodiments, as shown in FIGS. 6 and 7, additional clamping and/or orientation features 430, 530 can be included in the engagement area 218, similar to that of protrusion 220. Clamping features 430, 530 can be included on each side of the engagement housing 200 to provide additional grip and stability for the grasping member, or as required by the given surgical robot, so that the robot interface can be made mistake-proof and set to the right orientation each use. The clamping features 430, 530 can be arranged within the engagement area 218 in any suitable pattern or orientation, for example, asymmetric, symmetric, or a combination of the two, to allow for "Poka-Yoking" during assembly and orientation. As shown in FIG. 6, the clamping features 430 can be parallel to one another, spaced apart from one another and can extend perpendicularly between the bounds of the cover 422. It is also possible, as shown in FIG. 7, for the clamping features 530 to meet the bounds of the cover 522 at a slanted angle, while maintaining the spacing between one another and maintaining a parallel relationship.

Figure 8:
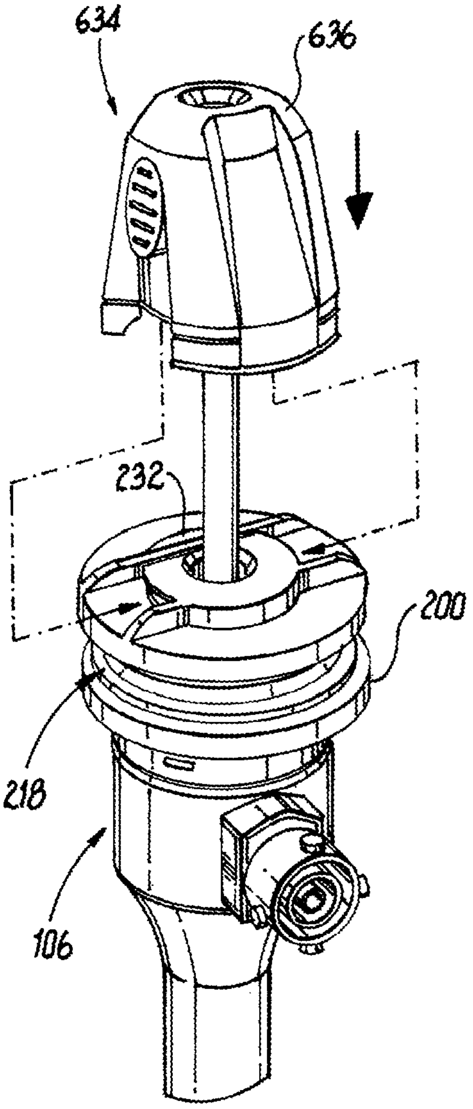
FIG. 8 is a side elevation view of an embodiment of an engagement housing of the access port of FIG. 1, showing insertion of an obturator through the engagement housing and the proximal housing portion.
Figure 9:
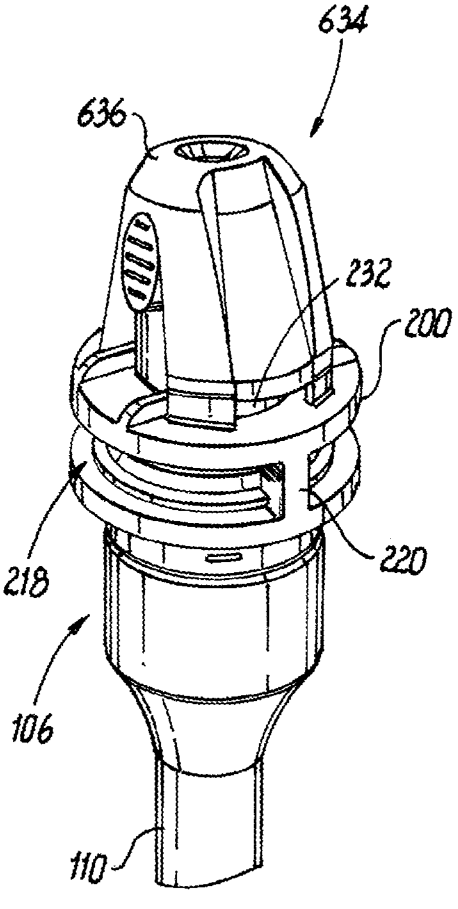
FIG. 9 is a side perspective view of the embodiment of FIG. 8, showing a mating of the obturator with the engagement housing.

In certain embodiments, such as shown in FIGS. 8 and 9, the engagement housing 200 further includes an attachment feature 232 configured to engage a proximal end 634 of a surgical instrument passing through the central lumen 108, such as obturator 636, for example as described in U.S. Pat. No. 9,545,264, issued Jan. 17, 2021, the entire content of which is incorporated herein by reference. Any suitable combination of embodiments as described herein with respect to FIGS. 1-9 is contemplated herein.

In accordance with at least one aspect of this disclosure, a gas sealed access port 100 can be as described in commonly assigned U.S. Pat. No. 8,795,223 issued Aug. 5, 2014, U.S. Pat. No. 10,905,463, issued Feb. 2, 2021. For example, the proximal housing portion of the gas sealed access port can include a central lumen providing gas sealed access to the surgical cavity, an inlet path for communicating with a source of pressurized gas, a tapered neck portion and an interior cavity accommodating an annular jet assembly for receiving pressurized gas from the inlet path to generate a gaseous seal within the tapered neck portion to maintain a stable pressure within the surgical cavity. An elongated tubular body extends from the tapered neck portion of the proximal housing in communication with the central lumen. An engagement housing, the same or similar to that as shown and described herein can be associated with the proximal housing portion.

In accordance with at least one aspect of this disclosure, an engagement housing 200 for an access port 100 for performing an endoscopic surgical procedure in a surgical cavity of a patient can include a cover 222, 322, 422, 522 configured to seat within a proximal housing of the access port. In embodiments, the cover can define an engagement area 218 disposed at least partially circumferentially around an outer periphery of the cover configured to releasably accept a grasping member of a surgical robot. The cover can also include one or more castellations 228, 328 extending distally therefrom configured to engage one or more detents in the proximal housing of the access port to retain the cover to the proximal housing. In embodiments, the engagement area may be generic, configured to accept any grasping member of any surgical robot (e.g., as shown in FIG. 6), or the engagement area may include one or more features, such as ridges, grooves, protrusions, or the like (e.g., 220, 430, 530) configured to conform to a specific grasping member of a specific surgical robot (e.g., as shown in FIGS. 3-7 and 9).

Figure 10:
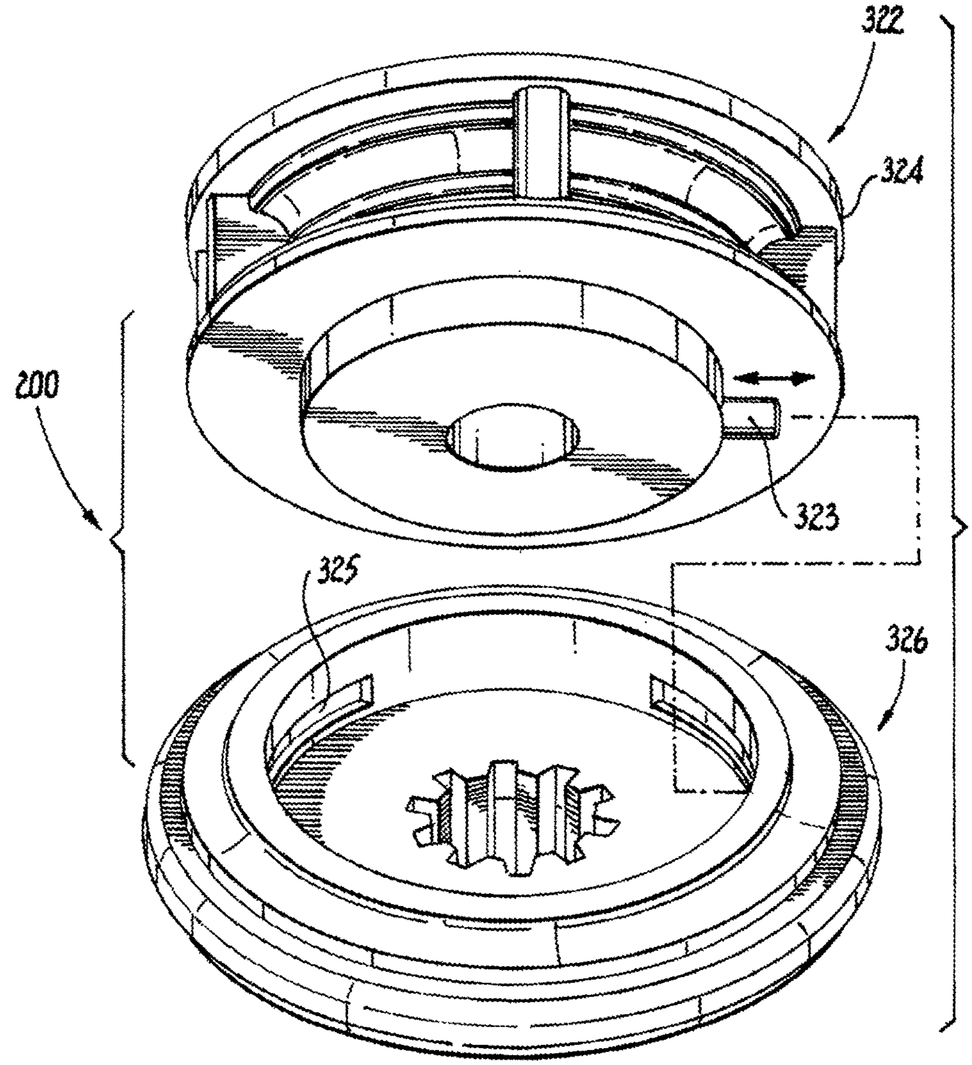
FIG. 10 is an exploded perspective view of the embodiment of FIG. 5, showing the upper and lower portions of the cover which can rotate relative to one another.
Figure 11:
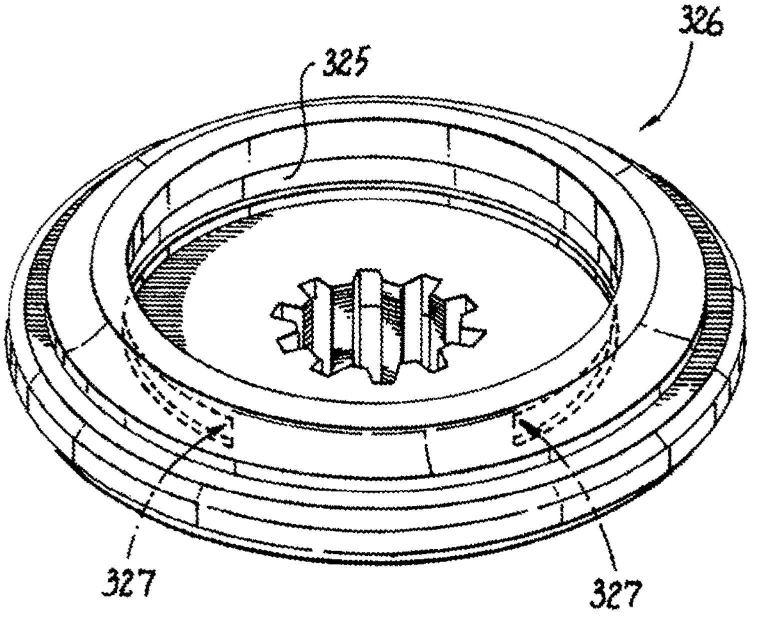
FIG. 11 is a perspective view of the lower portion of the cover of FIG. 10, showing the track guide for the detent pin to slide for relative rotation of the upper and lower portions of the cover.
Figure 12:
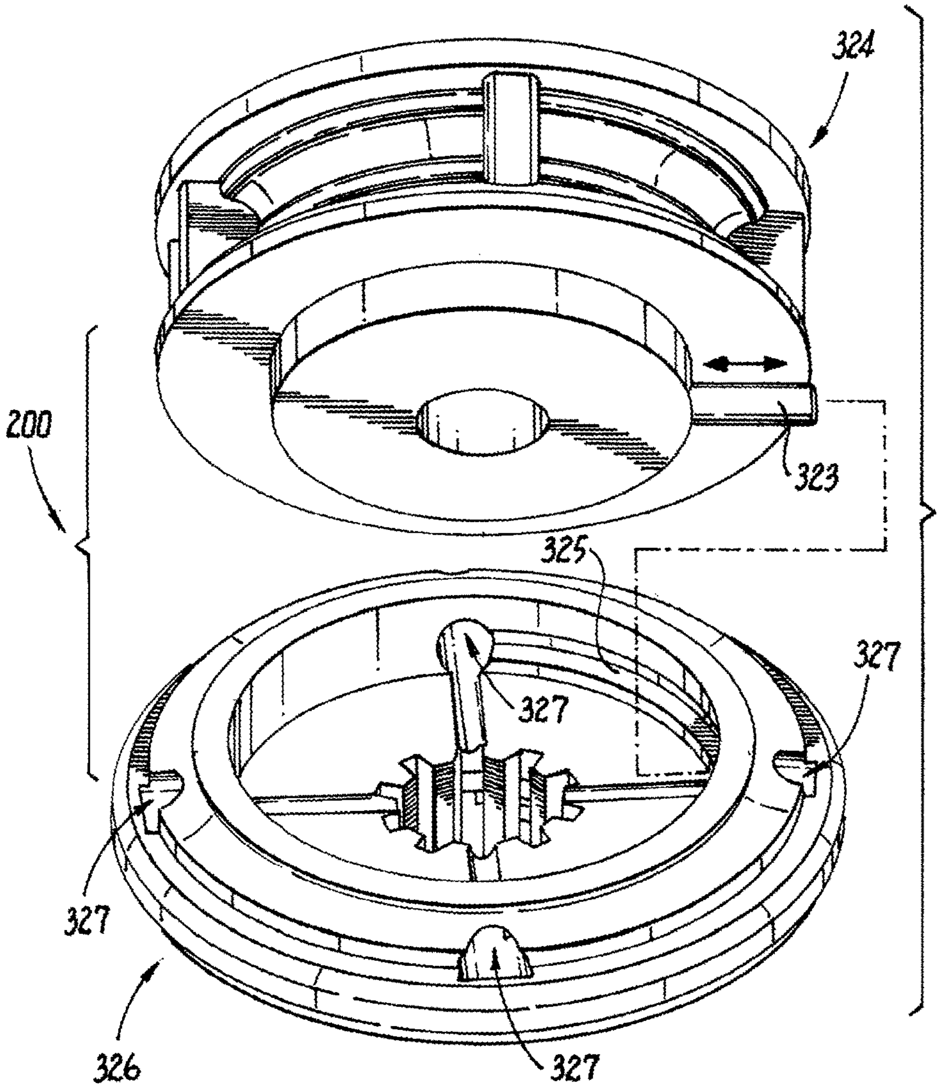
FIG. 12 is an exploded perspective of the embodiment of FIG. 5, showing another embodiment of the detent pin that can be actuated by a user.
Figure 13:
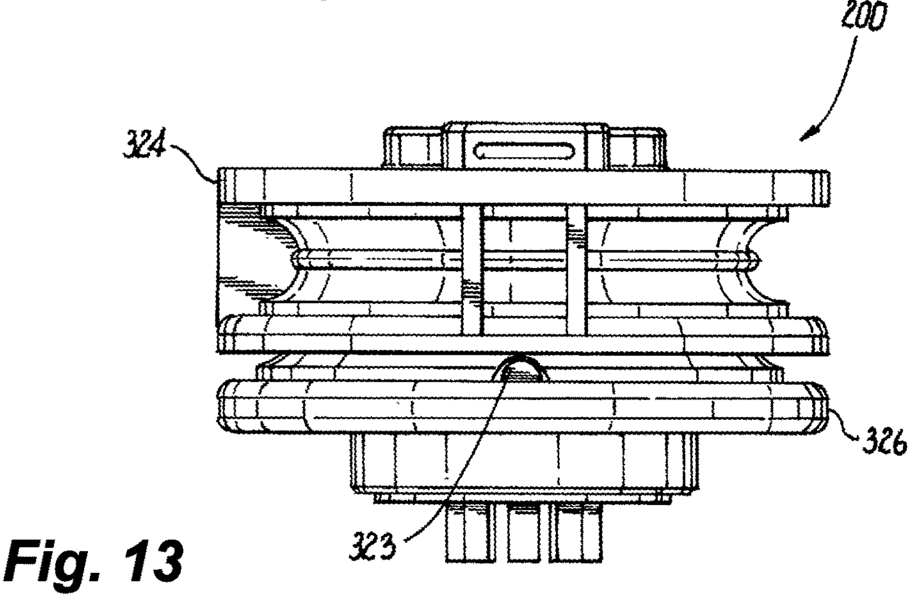
FIG. 13 is a perspective view of the embodiment of FIG. 12, showing the detent pin protruding from the lower portion of the cover.

With reference now to FIG. 10, The cover 322 of FIG. 5 is shown with the upper and lower portions 324, 326 separated. The detent pin 323 is spring loaded or otherwise biased to the position shown in FIG. 10, but can retract radially back into the upper portion 324 during assembly into the track guide 325 of the lower portion 326, which is labeled in FIG. 11. Once the upper and lower portions 324, 326 are assembled as indicated in FIG. 10, the detent pin 323 can slide to any position within the guide track 325 for relative rotation of the upper and lower portions 324, 326 as described above with respect to FIG. 5. The circumferential ends 327 of the guide track 325 serve as stops to limit the circumferential range of motion of the detent pin 323, limiting the range of motion for the relative rotation of the upper and lower portions 324, 326. The guide track 325 can extend circumferentially 90 degrees, 180 degrees, 270 degrees, or any suitable number of degrees as needed for a given application. Optionally, as shown in FIG. 12, the detent pin 323 can be made long enough to extend through stop bores 327 that extend radially through the outer wall of the lower portion 326. When the upper and lower portions 324, 326 are assembled as shown in FIG. 13, a user can press the detent pin 327 radially inward to rotate the upper and lower portions 324, 326 relative to one another with the detent pin 323 sliding in the guide track 325 until the detent pin 323 reaches the next stop bore 327, where the detent pin 323 will click radially outward through that new stop bore 327 to lock the rotational position of the upper and lower portions 324, 326. The radial motion of the detent pin 323 is indicated by the double arrow in FIG. 12. This can provide a locked rotational position with flexibility as to the choice of which rotational position, e.g. to help a surgeon position instruments and tubing for a procedure. The stop bores 327 can be positioned at 0 degrees, 90 degrees, 180 degrees, 270 degrees, or at any other suitable position or positions in the circumferential direction. The guide track 325 of FIG. 12 can optionally include ends as depicted in FIG. 11 in addition to the stop bores 327.

Embodiments, surgical robotics manufactures that do not manufacture their own cannulas or access ports utilize the access ports as described herein. Typical surgical robot grasping members are not designed to accommodate certain access ports. However systems and methods as shown and described herein can ensure the compatibility with most of the surgical robots.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The articles "a", "an", and "the" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

Any suitable combination(s) of any disclosed embodiments and/or any suitable portion(s) thereof are contemplated herein as appreciated by those having ordinary skill in the art in view of this disclosure.

The embodiments of the present disclosure, as described above and shown in the drawings, provide for improvement in the art to which they pertain. While the apparatus and methods of the subject disclosure have been shown and described, those skilled in the art will readily appreciate that changes and/or modifications may be made thereto without departing from the scope of the subject disclosure.

What is claimed is:

1. An access port for performing an endoscopic surgical procedure in a surgical cavity of a patient, comprising:

a proximal housing portion including a central lumen providing instrument access to the surgical cavity, wherein the proximal housing portion defines an interior plenum;

an engagement housing operatively associated with a proximal end of the proximal housing portion and having a concave circumferential engagement area formed therein that is adapted and configured to releasably accept a grasping member of a surgical robot, wherein the concave engagement area is defined between an upper annular engagement housing portion and a lower annular engagement housing portion, and wherein the upper annular engagement housing portion and the lower annular engagement housing portion are of equal outer diameter;

a seal housed within the interior plenum, wherein the engagement housing is proximal relative to the interior plenum and to the seal; and an elongated tubular body portion extending from the proximal housing portion in a distal direction, in communication with the central lumen.

2. The access port as recited in claim 1, wherein the upper cylindrical engagement housing portion further includes an attachment feature configured to engage a proximal end of an obturator passing through the central lumen.

3. The access port as recited in claim 1, wherein the proximal housing portion further includes a sound dampener disposed in the central lumen.

4. The access port as recited in claim 3, wherein the sound dampener includes foam material configured to dampen air sounds in the central lumen.

5. The access port as recited in claim 1, wherein the seal includes a ring jet assembly that is adapted and configured to accelerate pressurized gas delivered into the proximal housing portion to form a gaseous seal within a region of the tubular body portion so as to maintain a stable pressure in the surgical cavity.

6. The access port as recited in claim 1, wherein the engagement housing further includes one or more castellations extending distally therefrom configured to engage the proximal housing portion around the central lumen to retain the engagement housing to the proximal housing portion.

7. A gas sealed access port for performing an endoscopic surgical procedure in a surgical cavity of a patient, comprising:

a proximal housing portion including a central lumen providing gas sealed access to the surgical cavity, an inlet path for communicating with a source of pressurized gas, a tapered neck portion, an interior cavity accommodating a seal including an annular jet assembly for receiving pressurized gas from the inlet path to generate a gaseous seal within the tapered neck portion to maintain a stable pressure within the surgical cavity;

an engagement housing operatively associated with a proximal end of the proximal housing portion and having a concave circumferential engagement area formed therein that is adapted and configured to releasably accept a grasping member of a surgical robot, wherein the concave circumferential engagement area is defined between an upper annular engagement housing portion and a lower annular engagement housing portion, and wherein the upper annular engagement housing portion and the lower annular engagement housing portion are of equal outer diameter; and an elongated tubular body extending distally from the tapered neck portion of the proximal housing in communication with the central lumen.

* * * * *